US010015989B2

(12) United States Patent
Davis et al.

(10) Patent No.: US 10,015,989 B2
(45) Date of Patent: Jul. 10, 2018

(54) ONE-WAY VALVE FOR REFILLING AN AEROSOL DELIVERY DEVICE

(71) Applicant: R. J. REYNOLDS TOBACCO COMPANY, Winston-Salem, NC (US)

(72) Inventors: Michael F. Davis, Clemmons, NC (US); Percy D. Phillips, Pfafftown, NC (US); James William Rogers, Winston-Salem, NC (US); Noah M. Minskoff, Palo Alto, CA (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 107 days.

(21) Appl. No.: 15/008,323

(22) Filed: Jan. 27, 2016

(65) Prior Publication Data

US 2017/0208863 A1 Jul. 27, 2017

(51) Int. Cl.

*A24F 47/00* (2006.01)
*F16K 7/00* (2006.01)

(Continued)

(52) U.S. Cl.

CPC .......... *A24F 47/008* (2013.01); *A24F 47/002* (2013.01); *A61M 15/06* (2013.01);

(Continued)

(58) Field of Classification Search

CPC ..... A24F 47/008; A61M 11/00; A61M 15/042
See application file for complete search history.

(56) References Cited

U.S. PATENT DOCUMENTS

| | | | |
|---|---|---|---|
| 1,771,366 A | 7/1930 | Wyss et al. |
| 2,057,353 A | 10/1936 | Whittemore, Jr. |

(Continued)

FOREIGN PATENT DOCUMENTS

| | | |
|---|---|---|
| AU | 276250 | 7/1965 |
| CA | 2 641 869 | 5/2010 |

(Continued)

OTHER PUBLICATIONS

"Tesla's Valvular Conduit." Fluid Power Journal. Innovative Designs & Publishing, Inc., Oct. 23, 2013. Web. <http://fluidpowerjournal.com/2013/10/teslas-conduit/>.*

(Continued)

*Primary Examiner* — Jacob T Minskey
*Assistant Examiner* — Taryn Trace Willett
(74) *Attorney, Agent, or Firm* — Womble Bond Dickinson (US) LLP

(57) ABSTRACT

An aerosol delivery device having a check valve therein for use with refilling the aerosol delivery device is provided. The aerosol delivery device may comprise at least one housing defining a refillable reservoir for storing an aerosol precursor composition, and a heating element contained within the at least one housing and configured to activate and vaporize components of the aerosol precursor composition. A connector may be coupled to the at least one housing and sealably connectable with a container of aerosol precursor composition for refilling the reservoir. The connector may include a check valve configured to enable only a one-way flow of aerosol precursor composition from the container into the reservoir when the connector is sealably connected with the container.

12 Claims, 10 Drawing Sheets

(51) Int. Cl.

| | |
|---|---|
| ***F16K 15/14*** | (2006.01) |
| ***F16K 15/04*** | (2006.01) |
| ***F16K 15/00*** | (2006.01) |
| ***A61M 15/06*** | (2006.01) |
| *A61M 15/00* | (2006.01) |
| *A61M 11/04* | (2006.01) |

(52) U.S. Cl.
CPC ................ *F16K 7/00* (2013.01); *F16K 15/00* (2013.01); *F16K 15/044* (2013.01); *F16K 15/14* (2013.01); *A61M 11/042* (2014.02); *A61M 15/0021* (2014.02); *A61M 15/0091* (2013.01)

(56) References Cited

U.S. PATENT DOCUMENTS 2,104,266 A 1/1938 McCormick
3,045,671 A * 7/1962 Updegraff ................ A62B 7/00 128/205.21
3,200,819 A 8/1965 Gilbert
3,721,240 A * 3/1973 Tamburri ............. A61M 15/06 128/202.21
4,284,089 A 8/1981 Ray
4,303,083 A 12/1981 Burruss, Jr.
4,393,884 A * 7/1983 Jacobs .................. A24F 47/002 128/200.23
4,735,217 A 4/1988 Gerth et al.
4,848,374 A 7/1989 Chard et al.
4,907,606 A 3/1990 Lilja et al.
4,922,901 A 5/1990 Brooks et al.
4,945,931 A 8/1990 Gori
4,947,874 A 8/1990 Brooks et al.
4,947,875 A 8/1990 Brooks et al.
4,986,286 A 1/1991 Roberts et al.
5,019,122 A 5/1991 Clearman
5,042,510 A 8/1991 Curtiss et al.
5,060,671 A 10/1991 Counts et al.
5,093,894 A 3/1992 Deevi et al.
5,144,962 A 9/1992 Counts et al.
5,249,586 A 10/1993 Morgan et al.
5,261,424 A 11/1993 Sprinkel, Jr.
5,322,075 A 6/1994 Deevi et al.
5,353,813 A 10/1994 Deevi et al.
5,369,723 A 11/1994 Counts et al.
5,372,148 A 12/1994 McCafferty et al.
5,388,574 A 2/1995 Ingebrethsen et al.
5,408,574 A 4/1995 Deevi et al.
5,468,936 A 11/1995 Deevi et al.
5,498,850 A 3/1996 Das
5,515,842 A 5/1996 Ramseyer et al.
5,530,225 A 6/1996 Hajaligol
5,564,442 A 10/1996 MacDonald et al.
5,649,554 A 7/1997 Sprinkel et al.
5,666,977 A 9/1997 Higgins et al.
5,687,746 A 11/1997 Rose et al.
5,726,421 A 3/1998 Fleischhauer et al.
5,727,571 A 3/1998 Meiling et al.
5,743,251 A 4/1998 Howell et al.
5,799,663 A 9/1998 Gross et al.
5,819,756 A 10/1998 Mielordt
5,865,185 A 2/1999 Collins et al.
5,865,186 A 2/1999 Volsey, II
5,878,752 A 3/1999 Adams et al.
5,894,841 A 4/1999 Voges
5,934,289 A 8/1999 Watkins et al.
5,954,979 A 9/1999 Counts et al.
5,967,148 A 10/1999 Harris et al.
6,040,560 A 3/2000 Fleischhauer et al.
6,053,176 A 4/2000 Adams et al.
6,089,857 A 7/2000 Matsuura et al.
6,095,153 A 8/2000 Kessler et al.
6,125,853 A 10/2000 Susa et al.
6,155,268 A 12/2000 Takeuchi
6,164,287 A 12/2000 White
6,196,218 B1 3/2001 Voges
6,196,219 B1 3/2001 Hess et al.
6,598,607 B2 7/2003 Adiga et al.
6,601,776 B1 8/2003 Oljaca et al.
6,615,840 B1 9/2003 Fournier et al.
6,688,313 B2 2/2004 Wrenn et al.
6,772,756 B2 8/2004 Shayan
6,803,545 B2 10/2004 Blake et al.
6,854,461 B2 2/2005 Nichols
6,854,470 B1 2/2005 Pu
7,117,867 B2 10/2006 Cox et al.
7,293,565 B2 11/2007 Griffin et al.
7,513,253 B2 4/2009 Kobayashi et al.
7,775,459 B2 8/2010 Martens, III et al.
7,832,410 B2 11/2010 Hon
7,845,359 B2 12/2010 Montaser
7,896,006 B2 3/2011 Hamano et al.
8,127,772 B2 3/2012 Montaser
8,314,591 B2 11/2012 Terry et al.
8,365,742 B2 2/2013 Hon
8,402,976 B2 3/2013 Fernando et al.
8,499,766 B1 8/2013 Newton
8,505,548 B2 8/2013 Hearn
8,528,569 B1 9/2013 Newton
8,550,069 B2 10/2013 Alelov
8,757,169 B2 6/2014 Gysland
8,910,639 B2 12/2014 Chang et al.
8,955,522 B1 2/2015 Bowen et al.
9,022,039 B2 5/2015 Hearn
D769,519 S * 10/2016 Chen ............................ D27/101
9,668,522 B2 * 6/2017 Memari .................... B65B 3/04
2002/0146242 A1 10/2002 Vieira
2003/0226837 A1 12/2003 Blake et al.
2004/0118401 A1 6/2004 Smith et al.
2004/0129280 A1 7/2004 Woodson et al.
2004/0200488 A1 10/2004 Felter et al.
2004/0226568 A1 11/2004 Takeuchi et al.
2005/0016550 A1 1/2005 Katase
2006/0016453 A1 1/2006 Kim
2006/0196518 A1 9/2006 Hon
2007/0074734 A1 4/2007 Braunshteyn et al.
2007/0102013 A1 5/2007 Adams et al.
2007/0215167 A1 9/2007 Crooks et al.
2007/0267031 A1 11/2007 Hon
2008/0085103 A1 4/2008 Beland et al.
2008/0092912 A1 4/2008 Robinson et al.
2008/0257367 A1 10/2008 Paterno et al.
2008/0276947 A1 11/2008 Martzel
2008/0302374 A1 12/2008 Wengert et al.
2009/0095311 A1 4/2009 Hon
2009/0095312 A1 4/2009 Herbrich et al.
2009/0126745 A1 5/2009 Hon
2009/0188490 A1 7/2009 Hon
2009/0230117 A1 9/2009 Fernando et al.
2009/0255534 A1 10/2009 Paterno
2009/0272379 A1 11/2009 Thorens et al.
2009/0283103 A1 11/2009 Nielsen et al.
2009/0320863 A1 12/2009 Fernando et al.
2010/0043809 A1 2/2010 Magnon
2010/0083959 A1 4/2010 Siller
2010/0200006 A1 8/2010 Robinson et al.
2010/0229881 A1* 9/2010 Hearn ................... A24F 47/002 131/273
2010/0242974 A1 9/2010 Pan
2010/0242975 A1* 9/2010 Hearn ................... A24F 47/002 131/273
2010/0307518 A1 12/2010 Wang
2010/0313901 A1 12/2010 Fernando et al.
2011/0005535 A1 1/2011 Xiu
2011/0011396 A1 1/2011 Fang
2011/0036363 A1 2/2011 Urtsev et al.
2011/0036365 A1 2/2011 Chong et al.
2011/0087164 A1* 4/2011 Mosler .................. A61J 1/2089 604/87
2011/0094523 A1 4/2011 Thorens et al.
2011/0126848 A1 6/2011 Zuber et al.
2011/0155153 A1 6/2011 Thorens et al.
2011/0155718 A1 6/2011 Greim et al.
2011/0168194 A1 7/2011 Hon

(56) References Cited

U.S. PATENT DOCUMENTS

2011/0265806 A1 11/2011 Alarcon et al.
2011/0309157 A1 12/2011 Yang et al.
2011/0315152 A1* 12/2011 Hearn .................. A24F 47/002 131/273
2012/0042885 A1 2/2012 Stone et al.
2012/0060853 A1 3/2012 Robinson et al.
2012/0111347 A1 5/2012 Hon
2012/0132643 A1 5/2012 Choi et al.
2012/0167906 A1* 7/2012 Gysland ................ A24F 47/008 131/328
2012/0227752 A1 9/2012 Alelov
2012/0231464 A1 9/2012 Yu et al.
2012/0260927 A1 10/2012 Liu
2012/0279512 A1 11/2012 Hon
2012/0285476 A1 11/2012 Hon
2012/0318882 A1 12/2012 Abehasera
2013/0037041 A1 2/2013 Worm et al.
2013/0037042 A1 2/2013 Hearn et al.
2013/0056013 A1 3/2013 Terry et al.
2013/0081625 A1 4/2013 Rustad et al.
2013/0081642 A1 4/2013 Safari
2013/0087160 A1* 4/2013 Gherghe ............... A24F 47/008 131/329
2013/0192618 A1 8/2013 Li et al.
2013/0192619 A1 8/2013 Tucker et al.
2013/0213420 A1 8/2013 Hon
2013/0255702 A1 10/2013 Griffith, Jr. et al.
2013/0306084 A1 11/2013 Flick
2013/0319439 A1 12/2013 Gorelick et al.
2013/0340750 A1 12/2013 Thorens et al.
2013/0340775 A1 12/2013 Juster et al.
2014/0000638 A1 1/2014 Sebastian et al.
2014/0060554 A1 3/2014 Collett et al.
2014/0060555 A1 3/2014 Chang et al.
2014/0076310 A1* 3/2014 Newton ................ A61M 15/06 128/202.21
2014/0096781 A1 4/2014 Sears et al.
2014/0096782 A1 4/2014 Ampolini et al.
2014/0109921 A1 4/2014 Chen
2014/0123989 A1* 5/2014 LaMothe .............. A24F 47/008 131/328
2014/0157583 A1 6/2014 Ward et al.
2014/0209105 A1 7/2014 Sears et al.
2014/0253144 A1 9/2014 Novak et al.
2014/0261408 A1 9/2014 DePiano et al.
2014/0261486 A1 9/2014 Potter et al.
2014/0261487 A1 9/2014 Chapman et al.
2014/0261495 A1 9/2014 Novak et al.
2014/0270727 A1 9/2014 Ampolini et al.
2014/0270729 A1 9/2014 DePiano et al.
2014/0270730 A1 9/2014 DePiano et al.
2014/0283946 A1* 9/2014 Kribs ..................... B65D 47/06 141/2
2014/0307032 A1 10/2014 Xie et al.
2014/0345631 A1 11/2014 Bowen et al.
2015/0040929 A1 2/2015 Hon
2015/0053217 A1 2/2015 Steingraber et al.
2015/0097513 A1 4/2015 Liberti et al.
2015/0117841 A1* 4/2015 Brammer ................. H05B 3/02 392/387
2015/0128974 A1 5/2015 Hon
2015/0144145 A1 5/2015 Chang et al.
2015/0231108 A1 8/2015 Hearn et al.
2015/0245654 A1 9/2015 Memari et al.
2015/0257446 A1* 9/2015 Chung .................. A24F 47/008 131/329
2015/0282530 A1* 10/2015 Johnson ................ A24F 47/008 392/387
2015/0342258 A1* 12/2015 Chen ........................ H05B 3/06 131/329
2016/0095355 A1* 4/2016 Hearn ................... A24F 47/008 131/273
2016/0120227 A1* 5/2016 Levitz ................... A24F 47/008 219/386
2016/0128384 A1* 5/2016 Luciani ................. A24F 47/008 131/329
2016/0270446 A1* 9/2016 Shenkal ................ A24F 47/008
2016/0332754 A1* 11/2016 Brown ....................... B65B 3/10
2017/0013880 A1* 1/2017 O'Brien ................ A24F 47/008
2017/0086502 A1* 3/2017 Hearn ................... A24F 47/008
2017/0231274 A1* 8/2017 Davis .................... A24F 47/008 141/2
2017/0290368 A1* 10/2017 Hearn ................... A24F 47/002
2018/0044162 A1* 2/2018 Scott .................... B67D 7/0294

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| CN | 204682530 U | 10/2015 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| GB | 2469850 | 11/2010 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2013/089551 | 6/2013 |
| WO | WO 2014/155089 | 10/2014 |
| WO | WO 2014/155090 | 10/2014 |
| WO | WO 2014/155092 | 10/2014 |
| WO | WO 2014/155095 | 10/2014 |
| WO | WO 2015/157224 | 10/2015 |

OTHER PUBLICATIONS

International Search Report dated Apr. 13, 2017 for International Application No. PCT/IB2017/050424.

* cited by examiner

```
                            ┌─────────┐
                            │  START  │
                            └────┬────┘
                                 │
                                 ▼
┌──────────────────────────────────────────────────────────────────────┐
│  SEALABLY CONNECTING A CONNECTOR OF THE AEROSOL DELIVERY DEVICE      │
│  WITH A CONTAINER OF AEROSOL PRECURSOR COMPOSITION FOR REFILLING     │
│  THE RESERVOIR, THE CONNECTOR INCLUDING A CHECK VALVE CONTROLLING    │
│  FLOW OF AEROSOL PRECURSOR COMPOSITION FROM THE CONTAINER INTO THE   │
│  RESERVOIR WHEN THE CONNECTOR IS SEALABLY CONNECTED WITH THE         │
│                            CONTAINER                                  │
│                              902                                      │
└──────────────────────────────────┬───────────────────────────────────┘
                                   │
                                   ▼
┌──────────────────────────────────────────────────────────────────────┐
│  TRANSFERRING AEROSOL PRECURSOR COMPOSITION FROM THE CONTAINER        │
│  THROUGH THE CHECK VALVE AND INTO THE RESERVOIR TO THEREBY REFILL THE │
│                            RESERVOIR                                  │
│                              904                                      │
└──────────────────────────────────┬───────────────────────────────────┘
                                   │
                                   ▼
                            ┌─────────┐
                            │   END   │
                            └─────────┘
```

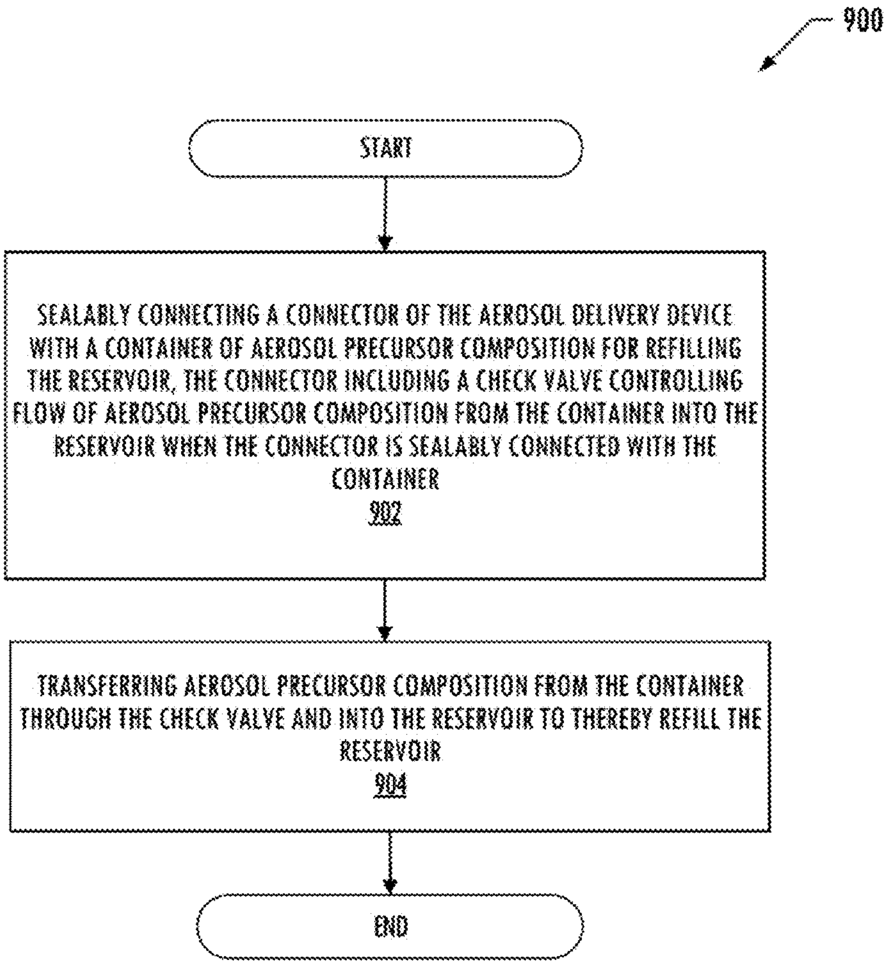

FIG. 9

ONE-WAY VALVE FOR REFILLING AN AEROSOL DELIVERY DEVICE

TECHNOLOGICAL FIELD

The present disclosure relates to aerosol delivery devices such as smoking articles that may utilize electrically generated heat for the production of aerosol (e.g., smoking articles commonly referred to as electronic cigarettes). The smoking articles may be configured to heat the aerosol precursor, which may incorporate materials that may be made or derived from tobacco or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar or pipe smoking, but without delivering considerable quantities of incomplete combustion and pyrolysis products that result from the burning of tobacco. To this end, there have been proposed numerous smoking products, flavor generators and medicinal inhalers that utilize electrical energy to vaporize or heat a volatile material, or attempt to provide the sensations of cigarette, cigar or pipe smoking without burning tobacco to a significant degree. See, for example, the various alternative smoking articles, aerosol delivery devices and heat generating sources set forth in the background art described in U.S. Pat. No. 7,726,320 to Robinson et al. and U.S. Pat. No. 8,881,737 to Collett et al., which are incorporated herein by reference. See also, for example, the various types of smoking articles, aerosol delivery devices and electrically-powered heat generating sources referenced by brand name and commercial source in U.S. Pat. Pub. No. 2015/0216232 to Bless et al., which is incorporated herein by reference. Additionally, various types of electrically powered aerosol and vapor delivery devices also have been proposed in U.S. Pat. Pub. No. 2014/0096781 to Sears et al. and U.S. Pat. Pub. No. 2014/0283859 to Minskoff et al., as well as U.S. patent application Ser. No. 14/282,768 to Sears et al., filed May 20, 2014; Ser. No. 14/286,552 to Brinkley et al., filed May 23, 2014; Ser. No. 14/327,776 to Ampolini et al., filed Jul. 10, 2014; Ser. No. 14/465,167 to Worm et al., filed Aug. 21, 2014; all of which are incorporated herein by reference.

SUMMARY OF THE DISCLOSURE

The present disclosure relates to aerosol delivery devices, methods of forming such devices, and elements of such devices. The present disclosure thus includes, without limitation, the following example implementations. In some example implementations, an aerosol delivery device is provided that includes at least one housing coupled to a connector, and a heating element contained within the housing. The housing defines a refillable reservoir for storing an aerosol precursor composition. The heating element is configured to activate and vaporize components of the aerosol precursor composition in response to a flow of air through at least a portion of the at least one housing. The air is combinable with a thereby formed vapor to form an aerosol. The connector is sealably connectable with a container of aerosol precursor composition for refilling the reservoir. The connector includes a check valve configured to control a flow of aerosol precursor composition from the container into the reservoir when the connector is sealably connected with the container.

In some example implementations of the aerosol delivery device of any preceding or any subsequent example implementation, or any combination thereof, the connector includes a body integral with or coupled to the check valve in which the body defines an airflow port for the flow of air through the connector from at least the portion of the at least one housing.

In some example implementations of the aerosol delivery device of any preceding or any subsequent example implementation, or any combination thereof, the check valve is a diaphragm check valve including a flexible diaphragm sized to fit an opening of the reservoir. The diaphragm defines a naturally-closed passageway that is configured to flex open and thereby allow through the passageway, the flow of aerosol precursor composition in response to at least a threshold positive pressure differential on a container-facing side of the flexible diaphragm when the connector is sealably connected with the container.

In some example implementations of the aerosol delivery device of the preceding or any subsequent example implementation, or any combination thereof, the check valve includes a valve member movable by the container to open a passageway and thereby allow through the passageway, the flow of aerosol precursor composition when the connector is sealably connected with the container.

In some example implementations of the aerosol delivery device of any preceding or any subsequent example implementation, or any combination thereof, the check valve includes a spring-loaded valve member configured to open a passageway and thereby allow through the passageway, the flow of aerosol precursor composition when the connector is sealably connected with the container.

In some example implementations of the aerosol delivery device of any preceding or any subsequent example implementation, or any combination thereof, the check valve is a Tesla valve or series of Tesla valves defining a channel configured to allow the flow of aerosol precursor composition in only one direction, from the container into the reservoir.

In some example implementations of the aerosol delivery device of any preceding or any subsequent example implementation, or any combination thereof, the connector further includes a slot mateable with a matching tab of the at least one housing to guide the connector into alignment with the at least one housing for coupling therewith.

In some example implementations of the aerosol delivery device of any preceding or any subsequent example implementation, or any combination thereof, the aerosol delivery device further comprises a mouthpiece removably coupled to the at least one housing over the connector such that the connector is exposed upon removal of the mouthpiece.

In some example implementations, a method of refilling an aerosol delivery device with aerosol precursor composition is provided. The aerosol delivery device may include at least one housing defining a refillable reservoir for storing aerosol precursor composition, and include a heating element configured to activate and vaporize components of the aerosol precursor composition stored in the reservoir in response to a flow of air through at least a portion of the at least one housing. The air is combinable with a thereby formed vapor to form an aerosol. The method includes sealably connecting a connector of the aerosol delivery device with a container of aerosol precursor composition for refilling the reservoir. The connector includes a check valve controlling flow of aerosol precursor composition from the container into the reservoir when the connector is sealably connected with the container. The method also includes transferring aerosol precursor composition from the container through the check valve and into the reservoir to thereby refill the reservoir.

In some example implementations of the method of any preceding or any subsequent example implementation, or any combination thereof, the connector includes a body integral with or coupled to the check valve in which the body defines an airflow port for the flow of air through the connector from at least the portion of the at least one housing.

In some example implementations of the method of any preceding or any subsequent example implementation, or any combination thereof, the check valve is a diaphragm check valve including a flexible diaphragm sized to fit an opening of the reservoir and defining a naturally-closed passageway, and transferring aerosol precursor composition includes causing at least a threshold positive pressure differential on a container-facing side of the flexible diaphragm to thereby cause the passageway to flex open and thereby allow through the passageway, the flow of aerosol precursor composition.

In some example implementations of the method of the preceding or any subsequent example implementation, or any combination thereof, the check valve includes a movable valve member, and sealably connecting the connector with the container includes the container moving the valve member to open a passageway and thereby allow through the passageway, the flow of aerosol precursor composition when the connector is sealably connected with the container.

In some example implementations of the method of any preceding or any subsequent example implementation, or any combination thereof, the check valve includes a spring-loaded valve member, and sealably connecting the connector with the container includes the valve member opening a passageway and thereby allowing through the passageway, the flow of aerosol precursor composition when the connector is sealably connected with the container.

In some example implementations of the method of any preceding or any subsequent example implementation, or any combination thereof, the check valve is a Tesla valve or series of Tesla valves defining a channel configured to allow the flow of aerosol precursor composition in only one direction, from the container into the reservoir, and transferring aerosol precursor composition includes transferring aerosol precursor composition from the container through the channel and into the reservoir.

In some example implementations of the method of any preceding or any subsequent example implementation, or any combination thereof, the aerosol delivery device further includes a mouthpiece removably coupled to the at least one housing over the connector, and the method further comprises removing the mouthpiece from the at least one housing such that the connector is exposed before sealably connecting the connector with the container.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE FIGURES

Figure 1A:
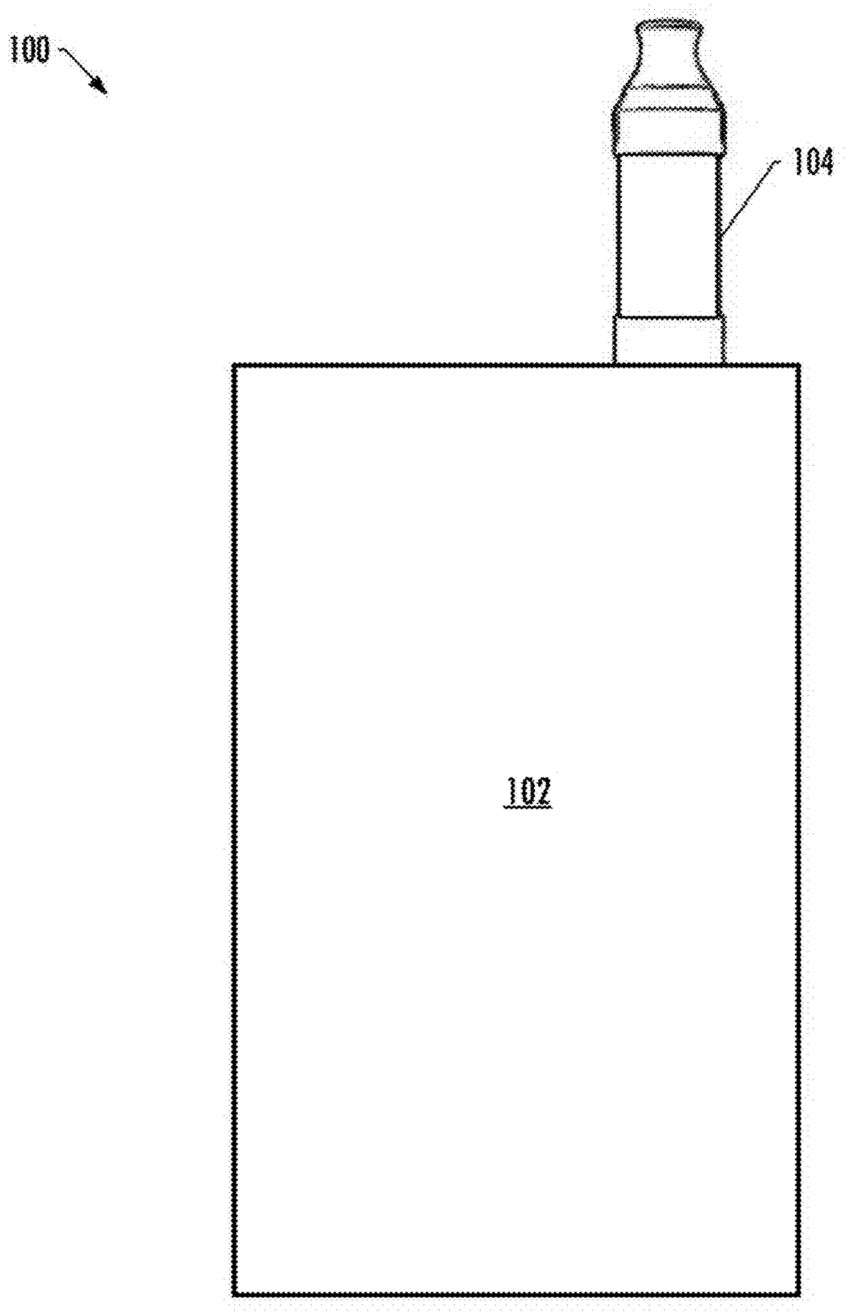
Figure 1B:
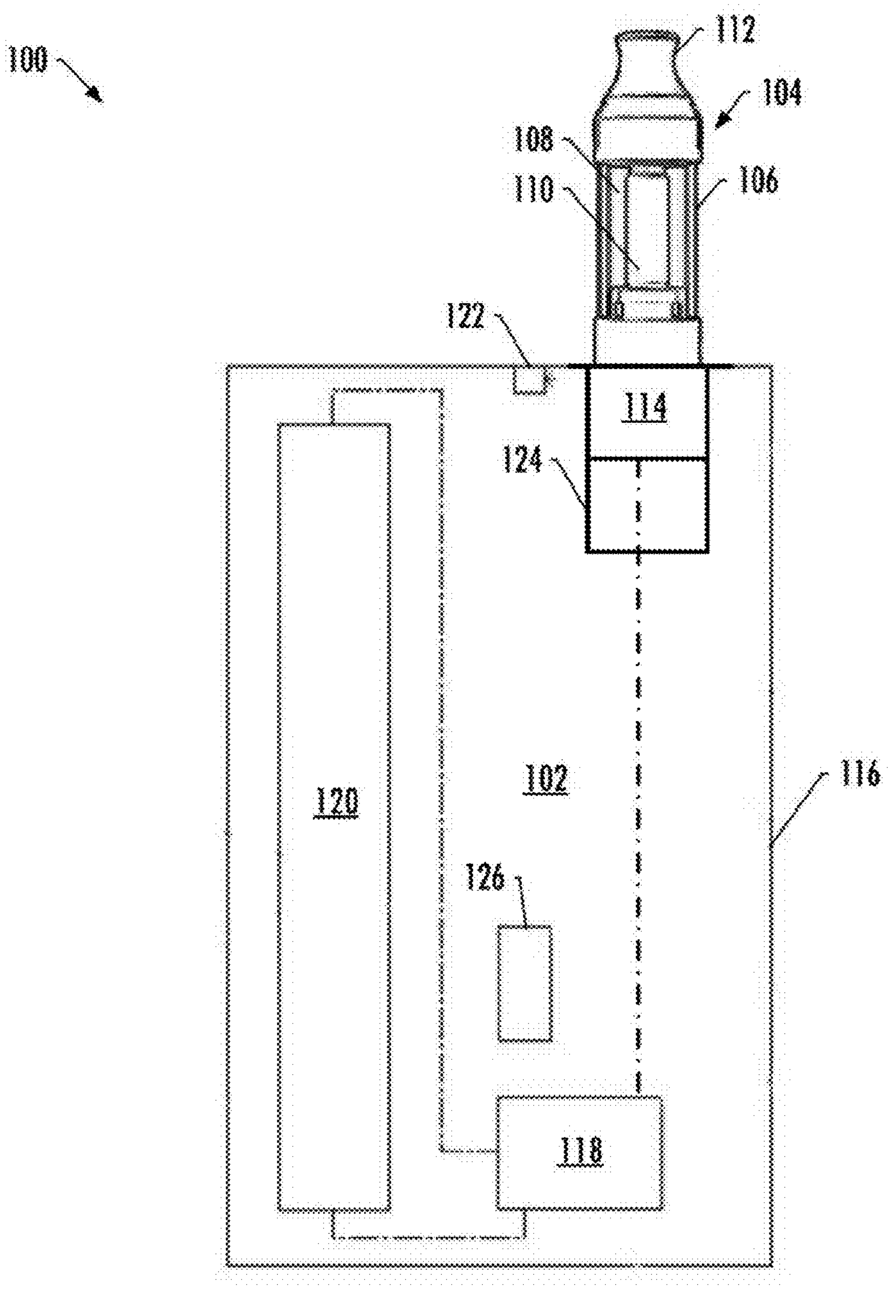
Figure 2:
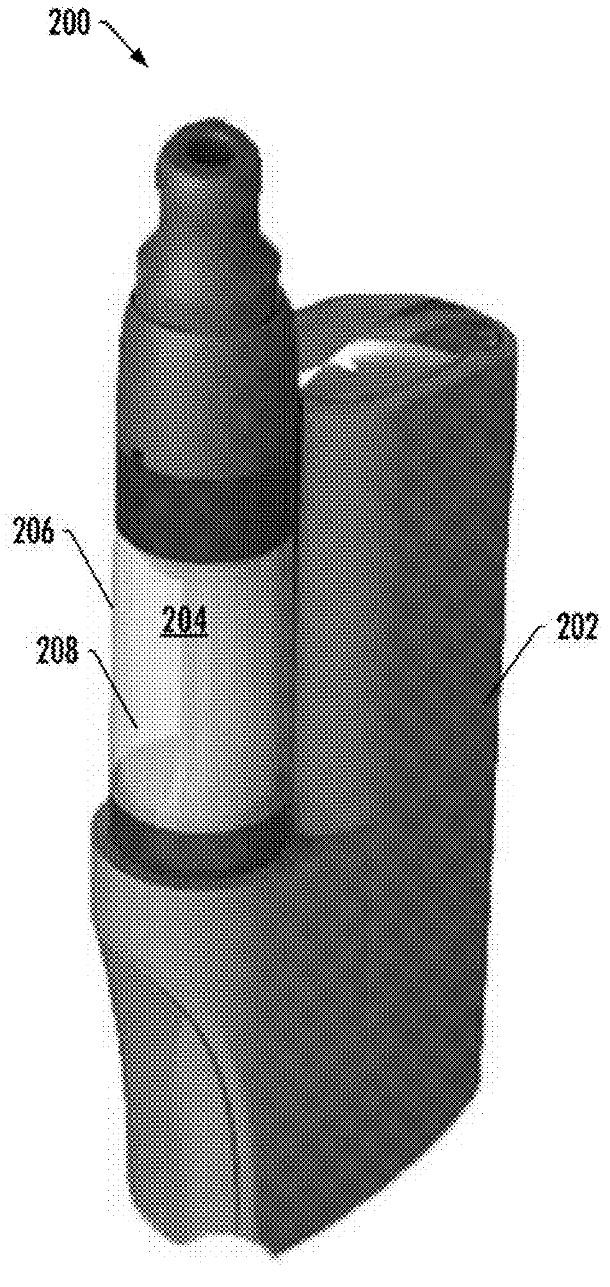
Figure 3:
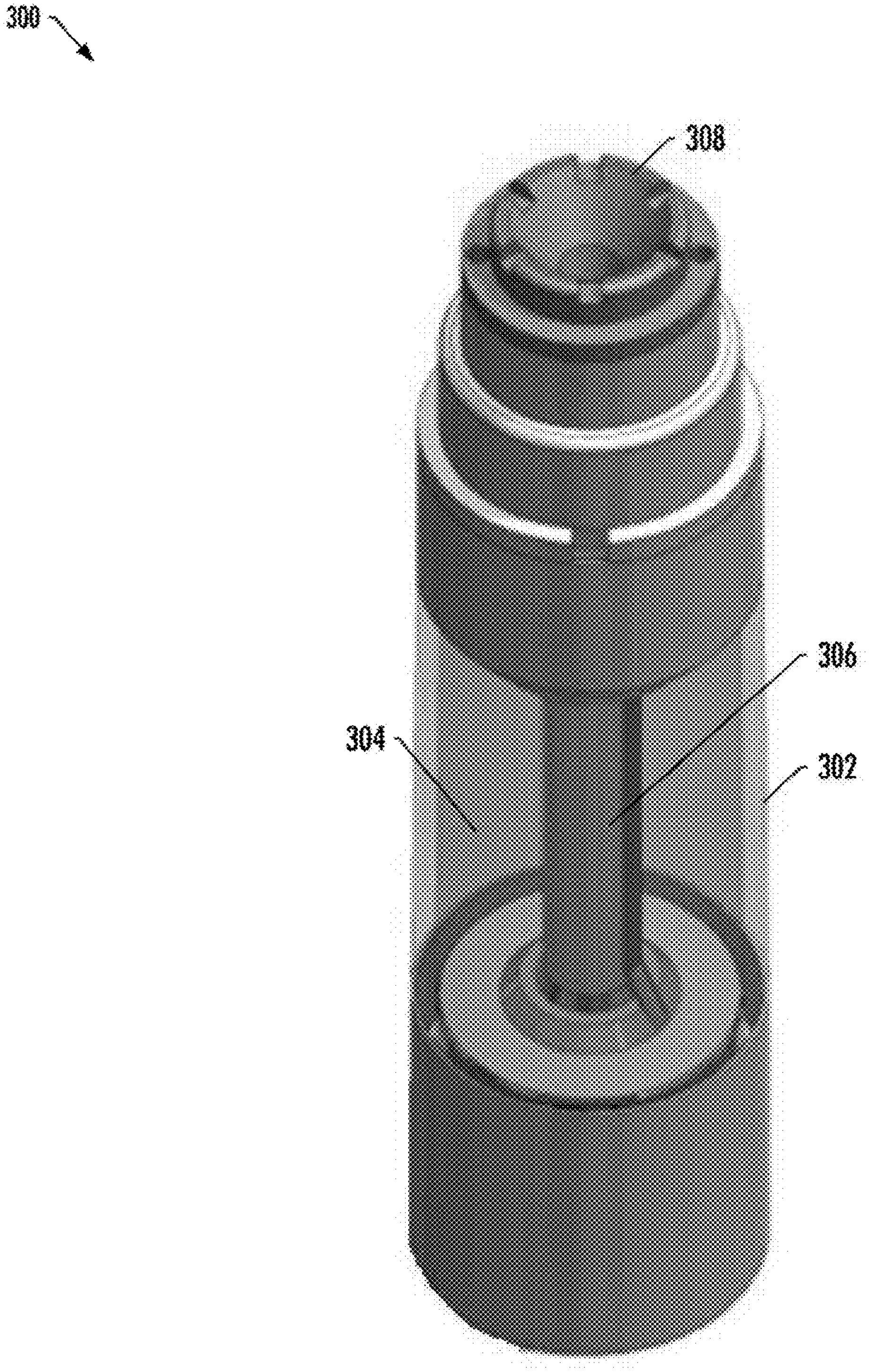
Figure 4:
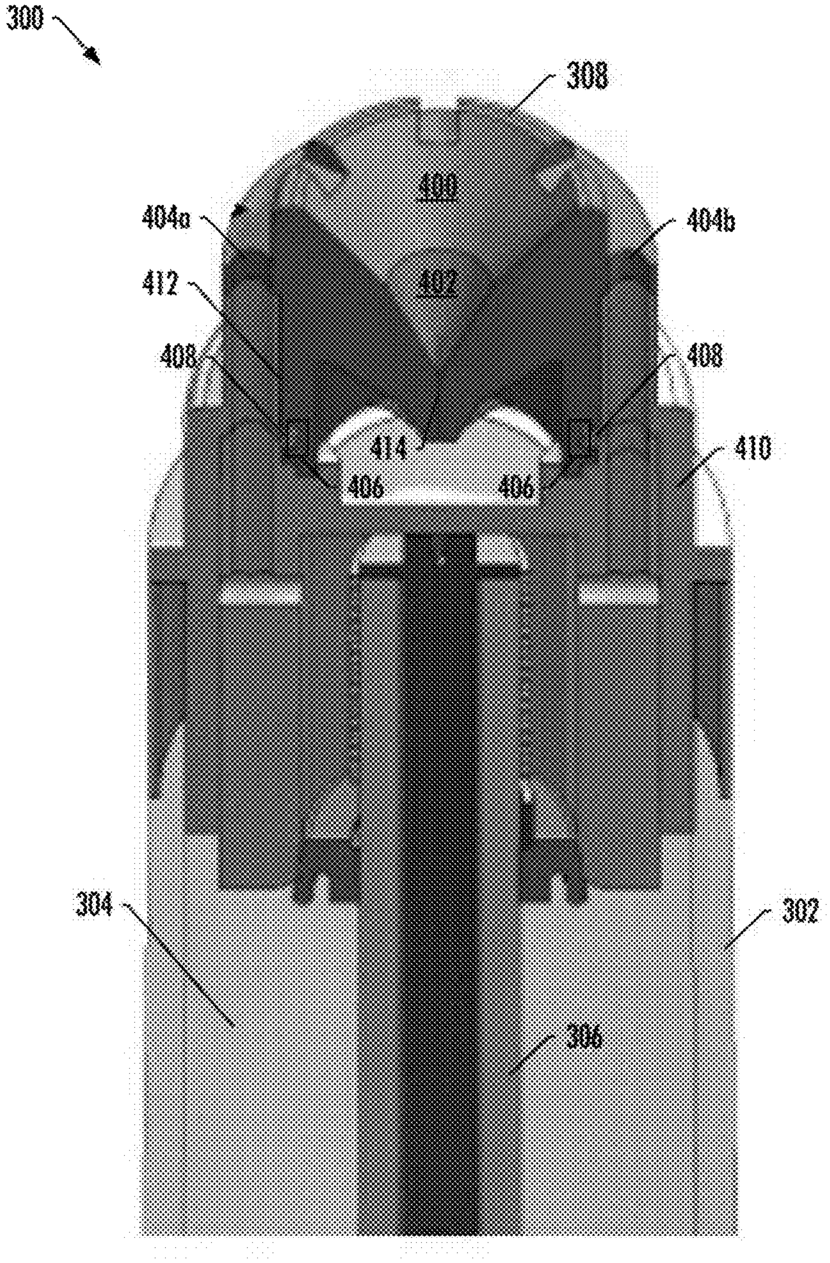
Figure 5B:
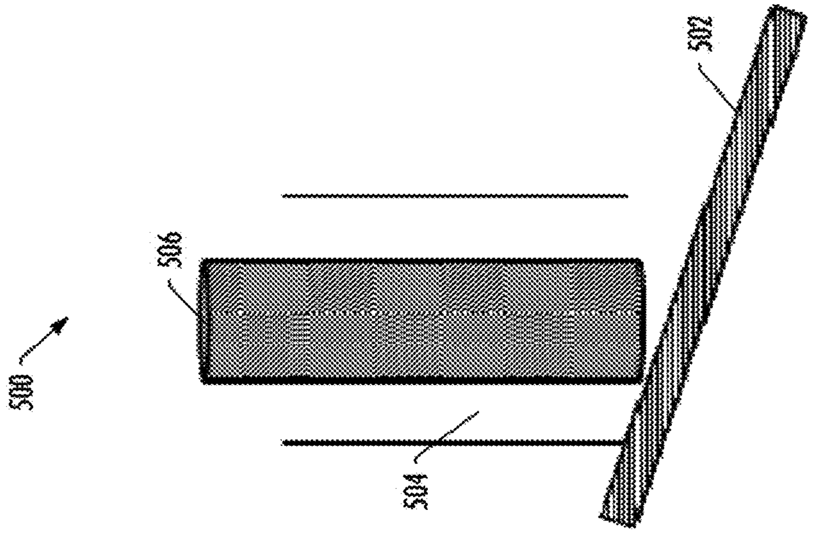
Figure 5A:
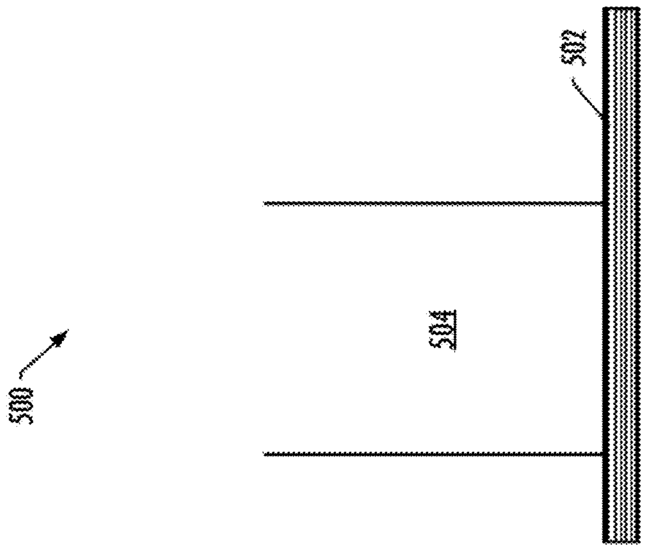
Figure 6B:
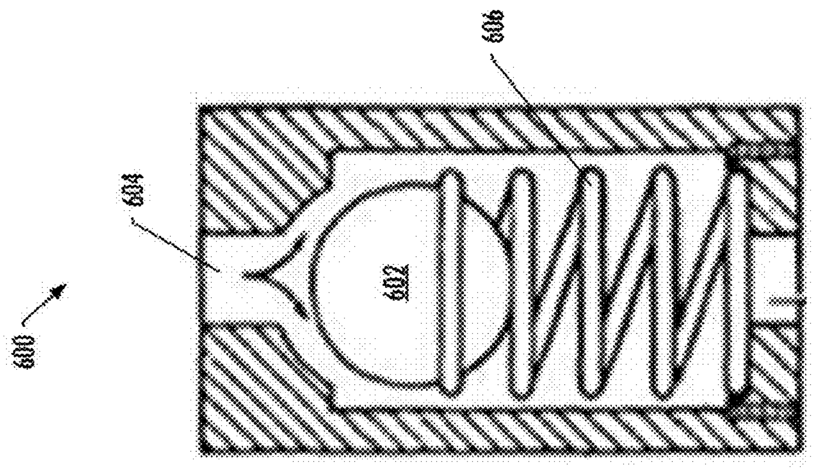
Figure 6A:
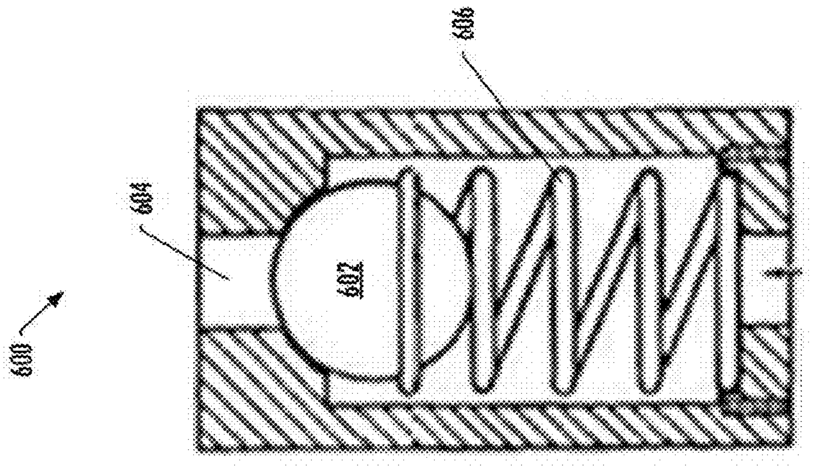
Figure 7:
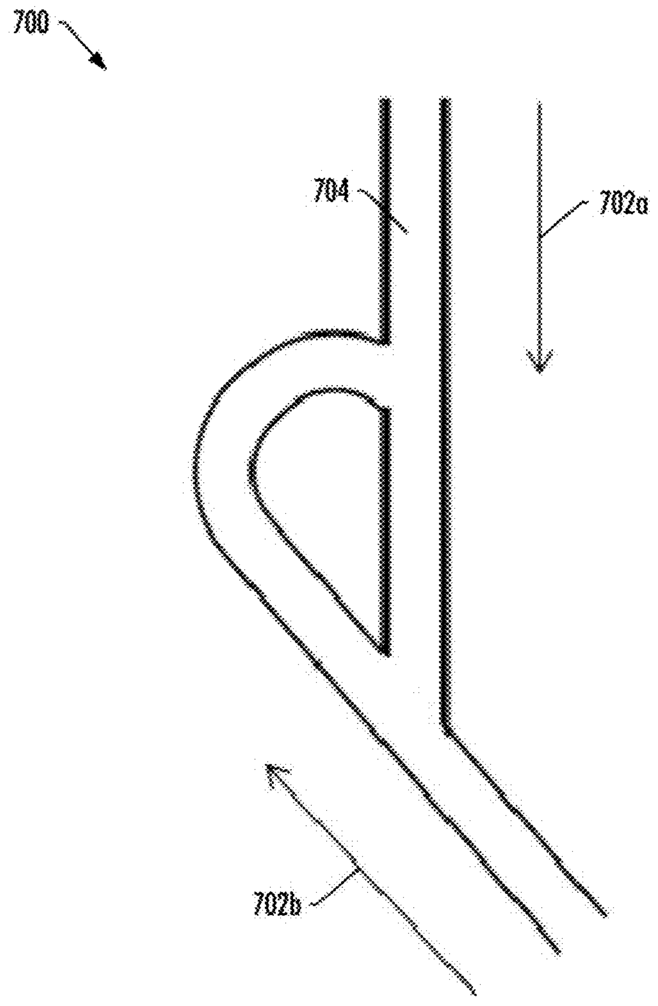
Figure 8:
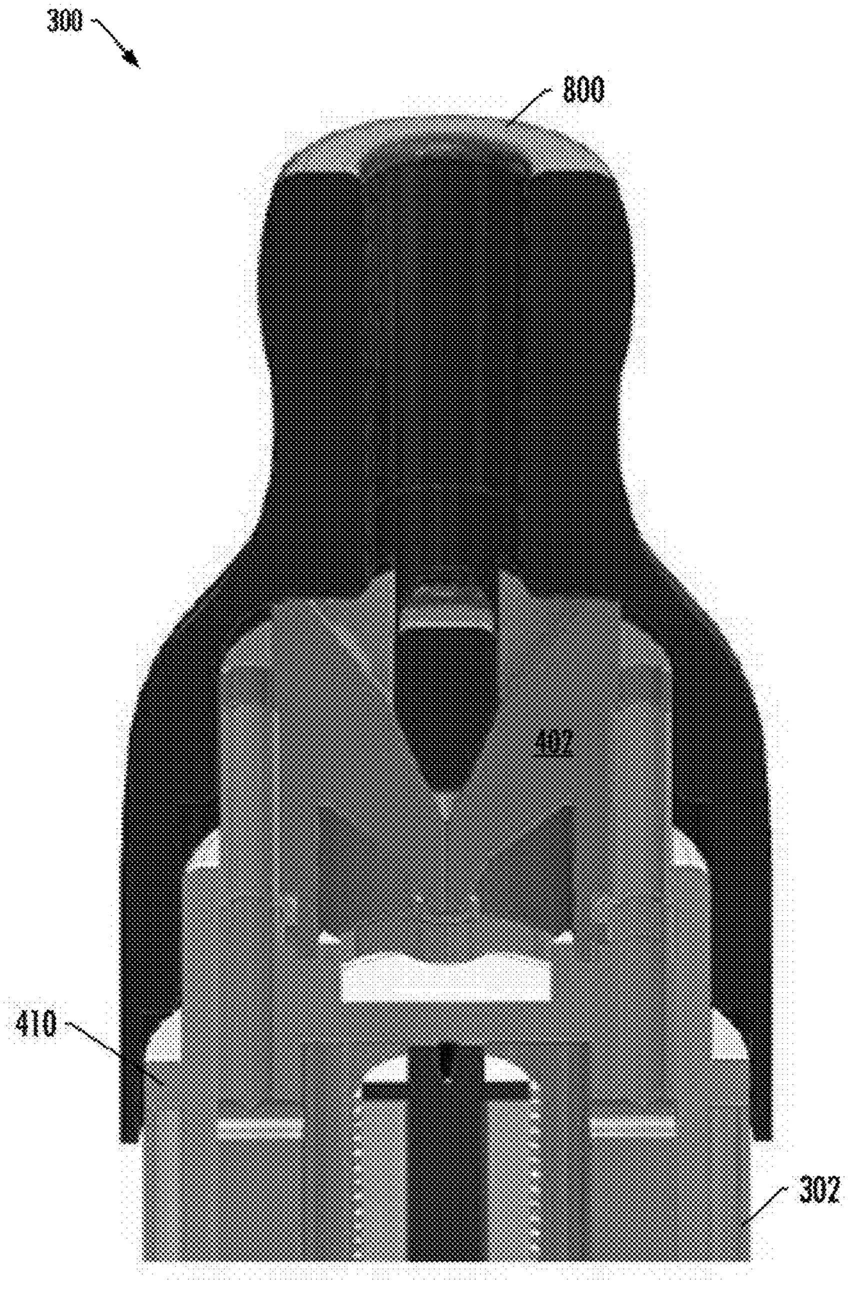

Having thus described the disclosure in the foregoing general terms, reference will now be made to the accompanying drawings, which are not necessarily drawn to scale, and wherein:

FIG. 1A illustrates a front view of aerosol delivery device including a tank coupled to a control body according to an example implementation of the present disclosure;

FIG. 1B illustrates a sectional view of the aerosol delivery device of FIG. 1;

FIG. 2 illustrates a perspective view of an aerosol delivery device, according to an example implementation of the present disclosure;

FIG. 3 illustrates a tank of an aerosol delivery device that may correspond to that of FIG. 2, which tank may include a one-way valve for refilling its reservoir, according to an example implementation of the present disclosure;

FIG. 4 illustrates a partially cut-away view of the tank of FIG. 3, according to an example implementation of the present disclosure;

FIGS. 5A and 5B illustrate a diaphragm check valve that may be useful for refilling the tank of an aerosol delivery device, according to an example implementation of the present disclosure;

FIGS. 6A and 6B illustrate a ball check valve that may be useful for refilling the tank of an aerosol delivery device, according to an example implementation of the present disclosure;

FIG. 7 illustrates a Tesla valve that may be useful for refilling the tank of an aerosol delivery device, according to an example implementation of the present disclosure;

FIG. 8 illustrates a partially cut-away view of the tank of FIG. 3 further including a removably coupled mouthpiece over its one-way valve, according to an example implementation of the present disclosure; and FIG. 9 illustrates various operations in a method of refilling an aerosol delivery device with aerosol precursor composition, according to an example implementation of the present disclosure.

DETAILED DESCRIPTION

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise.

As described hereinafter, example implementations of the present disclosure relate to aerosol delivery systems. Aerosol delivery systems according to the present disclosure use electrical energy to heat a material (preferably without combusting the material to any significant degree and/or without significant chemical alteration of the material) to form an inhalable substance; and components of such systems have the form of articles that most preferably are sufficiently compact to be considered hand-held devices. That is, use of components of preferred aerosol delivery systems does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery systems of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

Aerosol delivery systems of the present disclosure generally include a number of components provided within an outer body or shell, which may be referred to as a housing. The overall design of the outer body or shell can vary, and the format or configuration of the outer body that can define the overall size and shape of the aerosol delivery device can vary. Aerosol delivery devices are often configured in a manner that mimics aspects of certain traditional smoking devices such as cigarettes or cigars. In this regard, aerosol delivery devices typically define a substantially cylindrical configuration. Typically, an elongated body resembling the shape of a cigarette or cigar can be a formed from a single, unitary housing or the elongated housing can be formed of two or more separable bodies. For example, an aerosol delivery device can comprise an elongated shell or body that can be substantially tubular in shape and, as such, resemble the shape of a conventional cigarette or cigar. Aerosol delivery devices often include a control body and a cartridge which attach in an end-to-end relationship to define the substantially cylindrical configuration.

While such configurations may provide a look and feel that is similar to traditional smoking articles, these configurations may suffer from certain detriments. For example, cylindrically-configured aerosol delivery devices may not define attachment points usable to retain the aerosol delivery device in a desired position when not in use. Further, the cylindrical configuration may result in the mouthpiece being exposed to the surrounding environment and therefore susceptible to contamination. Accordingly, it may be desirable to provide aerosol delivery devices in configurations that differ from shapes associated with traditional smoking articles.

In one example, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., an accumulator such as a rechargeable battery and/or capacitor, and various electronics for controlling the operation of that article), and at the other end and removably coupleable thereto, an outer body or shell containing a disposable portion (e.g., a disposable flavor-containing cartridge).

Aerosol delivery systems of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microprocessor, individually or as part of a microcontroller), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined airflow path through the article such that aerosol generated can be withdrawn therefrom upon draw).

In various examples, an aerosol delivery device can comprise a reservoir configured to retain the aerosol precursor composition. The reservoir may be a void space for bulk fluid or particularly can be formed of a porous material (e.g., a rigid, porous material or primarily fibrous material) and thus may be referred to as a porous substrate.

A fibrous substrate useful as a reservoir in an aerosol delivery device can be a woven or nonwoven material formed of a plurality of fibers or filaments and can be formed of one or both of natural fibers and synthetic fibers. For example, a fibrous substrate may comprise a fiberglass material. In particular examples, a cellulose acetate material can be used. In other example implementations, a carbon material can be used. In further example implementations, organic cotton, polyethylene terephthalate, porous ceramic or glass, or porous sintered can be used. A reservoir may be substantially in the form of a container and may include a fibrous material included therein. In other implementations, the reservoir may be formed of a glass, plastic, or other materials not explicitly set forth herein.

In some implementations, the aerosol delivery device can include an indicator, which may comprise one or more light emitting diodes or a graphical user interface via a display. The indicator can be in communication with the control component through a connector circuit and illuminate, for example, during a user draw on the mouthend as detected by the flow sensor.

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure.

FIG. 1A illustrates a front view of an aerosol delivery device 100, and FIG. 1B illustrates a modified sectional view through the aerosol delivery device (collectively FIG. 1), according to an example implementation of the present disclosure. As illustrated, the aerosol delivery device may include a control body 102 and a tank 104. In particular, FIG. 1 illustrates the control body and the tank coupled to one another. The control body and the tank may be permanently or detachably aligned in a functioning relationship. Various mechanisms may connect the tank to the control body to result in a threaded engagement, a press-fit engagement, an interference fit, a magnetic engagement or the like. In some examples, the aerosol delivery device may be substantially rod-like, substantially tubular shaped, or substantially cylindrically shaped in some example implementations when the tank and the control body are in an assembled configuration. In other examples, further shapes and dimensions are encompassed—e.g., a rectangular or triangular cross-section, multifaceted shapes, or the like. The tank and control body may include a unitary housing or outer body or separate, respective housings or outer bodies, which may be formed of any of a number of different materials. The housing may be formed of any combination of suitable, structurally-sound materials. In some examples, the housing may be formed of at least one of a metal or alloy, such as stainless steel, aluminum or the like. Other suitable materials include various plastics (e.g., polycarbonate), metal-plating over plastic, glass, and the like.

In some example implementations, one or both of the control body 102 or the tank 104 of the aerosol delivery device 100 may be referred to as being disposable or as being reusable. The aerosol delivery device may include various other components disposed within the control body or tank or otherwise coupled thereto. These components may be distributed between the control body and the tank in any of various manners. For example, the control body may have a replaceable battery or removable battery or a rechargeable battery and thus may be combined with any type of recharging technology, including connection to a typical alternating current electrical outlet, connection to a car charger (i.e., a cigarette lighter receptacle), connection to a computer, such as through a universal serial bus (USB) cable or connector, or connection to a photovoltaic cell (sometimes referred to as a solar cell) or solar panel of solar cells. For example, an adaptor including a USB connector at one end and a control body connector at an opposing end is disclosed in U.S. Pat. Pub. No. 2014/0261495 to Novak et al., which is incorporated herein by reference in its entirety.

In one example implementation, the control body 102 and tank 104 forming the aerosol delivery device 100 may be permanently and/or removably coupled to one another. Examples of aerosol delivery devices that may be configured to be disposable and/or which may include first and second outer bodies that are configured for permanent coupling are disclosed in U.S. Pat. App. No. 2015/0216232 to Bless et al., which is incorporated herein by reference in its entirety. In another example implementation, the tank and control body may be configured in a single-piece, non-detachable form and may incorporate the components, aspects, and features disclosed herein. However, in another example implementation, the control body and tank may be configured to be separable such that, for example, the tank may be refilled or replaced.

FIG. 1B illustrates a more particular example of the aerosol delivery device 100 in which the components are representative of the components that may be present in a suitable control body 102 and a tank 104 and are not intended to limit the scope of control body and tank components that are encompassed by the present disclosure.

The tank 104 can be formed of a tank shell 106 enclosing a reservoir 108 configured to retain the aerosol precursor composition, and including a heater 110 (sometimes referred to as a heating element). In various configurations, this structure may be referred to as a cartridge; and accordingly, the terms "tank," "cartridge" and the like may be used interchangeably to refer to a shell or other housing enclosing a reservoir for aerosol precursor composition, and including a heater.

In some example, the reservoir 108 of the tank 104 may comprise a refillable reservoir. The reservoir may be configured to retain the aerosol precursor composition. In some example implementations, the reservoir particularly can be formed of a porous material (e.g., a fibrous material) and thus may be referred to as a porous substrate (e.g., a fibrous substrate). A fibrous substrate useful as a reservoir in an aerosol delivery device can be a woven or nonwoven material formed of a plurality of fibers or filaments and can be formed of one or both of natural fibers and synthetic fibers. For example, a fibrous substrate may comprise a fiberglass material. In particular examples, a cellulose acetate material can be used. In other example implementations, a carbon material can be used. A reservoir may be substantially in the form of a container and may include a fibrous material included therein. In other implementations, the reservoir may be formed of a glass, ceramic, plastic, or other materials not explicitly set forth herein.

The reservoir 108 may be in fluid communication with a liquid transport element adapted to wick or otherwise transport an aerosol precursor composition stored in the reservoir housing to the heater 110. In some examples, a valve may be positioned between the reservoir and heater, and configured to control an amount of aerosol precursor composition passed or delivered from the reservoir to the heater.

Various examples of materials configured to produce heat when electrical current is applied therethrough may be employed to form the heater 110. The heater in these examples may be resistive heating element such as a coil. Example materials from which the coil may be formed include Titanium (Ti), Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials (e.g., carbon-based foams and yarns) and ceramics (e.g., positive or negative temperature coefficient ceramics). The heating element may comprise a wire structure defining a mesh, screen or lattice structure positioned about the liquid transport element. Example materials from which the wire mesh, screen, or lattice that may be formed of, or include titanium, platinum, silver, palladium, Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials; and ceramic (e.g., a positive or negative temperature coefficient ceramic). Example implementations of heaters or heating members useful in aerosol delivery devices according to the present disclosure are further described below, and can be incorporated into devices described herein.

A mouthpiece 112 having an opening defined therein may be coupled to the tank shell 106 (e.g., at the mouthend) to allow for egress of formed aerosol from the tank 104.

The tank 104 may also include one or more electronic components, which may include an integrated circuit, a memory component, a sensor, or the like. The electronic components may be adapted to communicate with a control component of the control body and/or with an external device by wired or wireless means. The electronic components may be positioned anywhere within the tank or a base 114 thereof.

As illustrated in FIG. 1B, the control body 102 can be formed of a control body shell 116 that can include a control component 118 (e.g., a printed circuit board (PCB), an integrated circuit, a memory component, a microprocessor, individually or as part of a microcontroller, and the like), a power source 120, and one or more indicators 122 such as light-emitting diodes (LEDs), and such components can be variably aligned. The power source may include, for example, a battery (single-use or rechargeable), supercapacitor or the like. Further indicators (e.g., a haptic feedback component, an audio feedback component, or the like) can be included in addition to or as an alternative to the LED. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; and U.S. patent application Ser. No. 14/173,266, filed Feb. 5, 2014, to Sears et al.; which are incorporated herein by reference.

The control component 118 may be configured to direct electrical power from the power source 120 to the heater 110 to heat aerosol precursor composition retained in the tank 104 to produce a vapor, which may occur during a user draw on a mouthpiece 112 of the tank. The control component 118 may include a number of electronic components, and in some examples may be formed of an electronic or printed circuit board (PCB) that supports and electrically connects the electronic components. Examples of suitable electronic components include a microprocessor or processor core, an integrated circuit (IC), a memory, and the like.

In some examples, the control component 118 may include a microcontroller with an integrated processor core and memory, and which may further include one or more integrated input/output peripherals. In some examples, the control component may be coupled to a communication interface to enable wireless communication with one or more networks, computing devices or other appropriately-enabled devices. Examples of suitable communication interfaces are disclosed in U.S. patent application Ser. No. 14/638,562, filed Mar. 4, 2015, to Marion et al., the content of which is incorporated by reference in its entirety. And examples of suitable manners according to which the aerosol delivery device may be configured to wirelessly communicate are disclosed in U.S. patent application Ser. No. 14/327,776, filed Jul. 10, 2014, to Ampolini et al., and U.S. patent application Ser. No. 14/609,032, filed Jan. 29, 2015, to Henry, Jr. et al., each of which is incorporated herein by reference in its entirety.

The control body 102 and the tank 104 may include components adapted to facilitate a fluid engagement therebetween. As illustrated in FIG. 1B, the control body can include a connector 124. The base 114 of the tank can be adapted to engage the connector and can include a projection adapted to fit within the connector. Such engagement can facilitate a stable connection between the control body and the tank as well as establish an electrical connection between the battery 120 and control component 118 in the control body, and the heater 110 in the tank. Further, the control body shell 116 can include an air intake, which may be a notch in the shell where it connects to the connector that allows for passage of ambient air around the connector and into the shell where it then passes through the connector and into the tank through the projection.

A connector and a base useful according to the present disclosure are described in U.S. Pat. App. Pub. No. 2014/0261495 to Novak et al., which is incorporated herein by reference in its entirety. However, various other examples of structures, shapes and components may be employed to couple the base to the connector. In some examples the connection between the base of the tank 104 and the connector of the control body 102 may be substantially permanent, whereas in other examples the connection therebetween may be releasable such that, for example, the control body may be reused with one or more additional tanks that may be disposable and/or refillable.

The reservoir 108 illustrated in FIG. 1B can be a container or can be a reservoir, as presently described. For example, the reservoir can be substantially formed into the shape of a tube encircling the interior of the tank shell 106, in this example. An aerosol precursor composition can be retained in the reservoir. Liquid components, for example, can be retained by the reservoir. The reservoir can be in fluid connection with the liquid transport element. The liquid transport element can transport the aerosol precursor composition stored in the reservoir via capillary action to the heater 110 that is in the form of a metal wire coil in this example. As such, the heater is in a heating arrangement with the liquid transport element. Example implementations of reservoirs and transport elements useful in aerosol delivery devices according to the present disclosure are further described below, and such reservoirs and/or transport elements can be incorporated into devices as described herein. In particular, specific combinations of heating members and transport elements as further described below may be incorporated into devices.

In use, when a user draws on the aerosol delivery device 100, airflow is detected by a flow sensor, and the heater 110 is activated to vaporize components of the aerosol precursor composition. In some implementations, a manual button may be used exclusively, or in combination with a flow sensor, to activate the heater. Alternatively, the manual button may be depressed to activate the heater in lieu of a flow sensor. Drawing upon the mouthpiece 112 of the aerosol delivery device causes ambient air to enter the air intake and pass through the connector 124 and a central opening in a projection of the base 114. In the tank 104, the drawn air combines with the formed vapor to form an aerosol. The aerosol is whisked, aspirated or otherwise drawn away from the heater and out the opening in the mouthpiece of the aerosol delivery device.

An input element 126 may be included with the aerosol delivery device 100. The input element may be included to allow a user to control functions of the device and/or for output of information to a user. For example, a user may utilize the input element to vaporize an aerosol precursor composition and/or activate an on/off function. The input element may comprise a pushbutton or other switch configured to receive an input from a user. When the input element is actuated, the aerosol delivery device may produce an output corresponding to a status of the aerosol delivery device. For example, the aerosol delivery device may output sound, vibration, or light. Any component or combination of components may be utilized as an input for controlling the function of the device. For example, one or more pushbuttons may be used as described in U.S. patent application Ser. No. 14/193,961, filed Feb. 28, 2014, to Worm et al., which is incorporated herein by reference. Likewise, a touchscreen may be used as described in U.S. patent application Ser. No. 14/643,626, filed Mar. 10, 2015, to Sears et al., which is incorporated herein by reference. As a further example, components adapted for gesture recognition based on specified movements of the aerosol delivery device may be used as an input. See U.S. patent application Ser. No. 14/565,137, filed Dec. 9, 2014, to Henry et al., which is incorporated herein by reference.

In some example implementations, a computing device such as a mobile computer (e.g., smartphone, tablet computer) may be used as an input element in addition to or in lieu of an input element 126 on the aerosol delivery device itself. In particular, the aerosol delivery device 100 may be wired to the computer or other device, such as via use of a USB cord or similar protocol. The aerosol delivery device also may communicate with a computer or other device acting as an input via wireless communication. See, for example, the systems and methods for controlling a device via a read request as described in U.S. patent application Ser. No. 14/327,776, filed Jul. 10, 2014, to Ampolini et al., the disclosure of which is incorporated herein by reference. In such implementations, application software may be used in connection with the computing device to input control instructions to the aerosol delivery device, such control instructions including, for example, the ability to form an aerosol of specific composition by choosing the nicotine content and/or content of further flavors to be included.

In some examples, the aerosol delivery device 100 may include a number of additional hardware-implemented or software-controlled functions. For example, the aerosol delivery device may include a battery protection circuit configured to detect battery input, loads on the battery terminals, and charging input. The battery protection circuit may include short-circuit protection and under-voltage lock out. The aerosol delivery device may also include components for ambient temperature measurement, and its control component 118 may be configured to control at least one functional element to inhibit battery charging if the ambient temperature is below a certain temperature (e.g., 0° C.) or above a certain temperature (e.g., 45° C.) prior to start of charging or during charging.

Power delivery from the battery 120 may vary over the course of each puff on the device 100 according to a power control mechanism. The device may include a "long puff" safety timer such that in the event that a user or an inadvertent mechanism causes the device to attempt to puff continuously, the control component 118 may control at least one functional element to terminate the puff automatically after some period of time (e.g., four seconds). Further, the time between puffs on the device may be restricted to greater than a period of time (e.g., one hundred (100) milliseconds). A watchdog safety timer may automatically reset the aerosol delivery device if its control component or software running on it becomes unstable and does not service the timer within an appropriate time interval (e.g., eight seconds). Further safety protection may be provided in the event of a defective or otherwise failed flow sensor, such as by permanently disabling the aerosol delivery device in order to prevent inadvertent heating. A puffing limit switch may deactivate the device in the event of a pressure sensor fail causing the device to continuously activate without stopping after the four second maximum puff time.

The various components of an aerosol delivery device according to the present disclosure can be chosen from components described in the art and commercially available. Examples of batteries that can be used according to the disclosure are described in U.S. Pat. Pub. No. 2010/0028766 to Peckerar et al., the disclosure of which is incorporated herein by reference in its entirety.

The aerosol delivery device 100 most preferably incorporates the control component 118 or another control mechanism for controlling the amount of electric power to the heater 110 during draw. In some implementations, the control component may effect control of different power settings on the aerosol delivery device. For example, at least a low, medium, and high power setting may be controlled for adjusting aerosol production within the aerosol delivery device. Representative types of electronic components, structure and configuration thereof, features thereof, and general methods of operation thereof, are described in U.S. Pat. No. 4,735,217 to Gerth et al., U.S. Pat. No. 4,947,874 to Brooks et al., U.S. Pat. No. 5,372,148 to McCafferty et al., U.S. Pat. No. 6,040,560 to Fleischhauer et al., U.S. Pat. No. 7,040,314 to Nguyen et al., U.S. Pat. No. 8,205,622 to Pan, U.S. Pat. App. Pub. No. 2009/0230117 to Fernando et al., U.S. Pat. App. Pub. No. 2014/0060554 to Collet et al., U.S. Pat. App. Pub. No. 2014/0270727 to Ampolini et al., and U.S. patent application Ser. No. 14/209,191 to Henry et al., filed Mar. 13, 2014, all of which are incorporated herein by reference in their entireties.

The aerosol delivery device 100 can also incorporate the flow sensor or another sensor or detector for control of supply of electric power to the heater 110 when aerosol generation is desired (e.g., upon draw during use). As such, for example, there is provided a manner or method of turning off the power supply to the heating element when the aerosol delivery device is not be drawn upon during use, and for turning on the power supply to actuate or trigger the generation of heat by the heating element during draw. Additional representative types of sensing or detection mechanisms, structure and configuration thereof, components thereof, and general methods of operation thereof, are described in U.S. Pat. No. 5,261,424 to Sprinkel, Jr., U.S. Pat. No. 5,372,148 to McCafferty et al., and PCT Pat. App. Pub. No. WO 2010/003480 to Flick, all of which are incorporated herein by reference in their entireties.

Representative types of substrates, reservoirs or other components for supporting the aerosol precursor are described in U.S. Pat. No. 8,528,569 to Newton, U.S. Pat. App. Pub. No. 2014/0261487 to Chapman et al., U.S. patent application Ser. No. 14/011,992 to Davis et al., filed Aug. 28, 2013, and U.S. patent application Ser. No. 14/170,838 to Bless et al., filed Feb. 3, 2014, all of which are incorporated herein by reference in their entireties. Additionally, various wicking materials, and the configuration and operation of those wicking materials within certain types of electronic cigarettes, are set forth in U.S. Pat. App. Pub. No. 2014/0209105 to Sears et al., which is incorporated herein by reference in its entirety.

For aerosol delivery systems that are characterized as electronic cigarettes, the aerosol precursor composition most preferably incorporates tobacco or components derived from tobacco. In one regard, the tobacco may be provided as parts or pieces of tobacco, such as finely ground, milled or powdered tobacco lamina. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine).

The aerosol precursor composition, also referred to as a vapor precursor composition, may comprise a variety of components including, by way of example, a polyhydric alcohol (e.g., glycerin, propylene glycol, or a mixture thereof), nicotine, tobacco, tobacco extract, and/or flavorants. Various components that may be included in the aerosol precursor composition are described in U.S. Pat. No. 7,726,320 to Robinson et al., which is incorporated herein by reference in its entirety. Additional representative types of aerosol precursor compositions are set forth in U.S. Pat. No. 4,793,365 to Sensabaugh, Jr. et al., U.S. Pat. No. 5,101,839 to Jakob et al., U.S. Pat. No. 6,779,531 to Biggs et al., U.S. Pat. App. Pub. No. 2013/0008457 to Zheng et al., and *Chemical and Biological Studies on New Cigarette Prototypes that Heat Instead of Burn Tobacco*, R. J. Reynolds Tobacco Company Monograph (1988), all of which are incorporated herein by reference in their entireties.

Representative types of aerosol precursor components and formulations also are set forth and characterized in U.S. Pat. No. 7,217,320 to Robinson et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU™ product by Imperial Tobacco Group PLC, the MISTIC MENTHOL product by Mistic Ecigs, and the VYPE product by CN Creative Ltd. Also desirable are the so-called “smoke juices” for electronic cigarettes that have been available from Johnson Creek Enterprises LLC.

The amount of aerosol precursor that is incorporated within the aerosol delivery system is such that the aerosol generating piece provides acceptable sensory and desirable performance characteristics. For example, it is highly preferred that sufficient amounts of aerosol forming material (e.g., glycerin and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. Typically, the amount of aerosol precursor incorporated within the aerosol delivery system, and particularly within the aerosol generating piece, is less than about 5 g, generally less than about 2.5 g, often less than about 2 g and frequently less than about 1 g.

Additional representative types of components that yield visual cues or indicators may be employed in the aerosol delivery device 100, such as LEDs and related components, auditory elements (e.g., speakers), vibratory elements (e.g., vibration motors) and the like. Examples of suitable LED components, and the configurations and uses thereof, are described in U.S. Pat. No. 5,154,192 to Sprinkel et al., U.S. Pat. No. 8,499,766 to Newton, U.S. Pat. No. 8,539,959 to Scatterday, and U.S. patent application Ser. No. 14/173,266 to Sears et al., filed Feb. 5, 2014, all of which are incorporated herein by reference in their entireties.

Yet other features, controls or components that can be incorporated into aerosol delivery devices of the present disclosure are described in U.S. Pat. No. 5,967,148 to Harris et al., U.S. Pat. No. 5,934,289 to Watkins et al., U.S. Pat. No. 5,954,979 to Counts et al., U.S. Pat. No. 6,040,560 to Fleischhauer et al., U.S. Pat. No. 8,365,742 to Hon, U.S. Pat. No. 8,402,976 to Fernando et al., U.S. Pat. App. Pub. No. 2005/0016550 to Katase, U.S. Pat. App. Pub. No. 2010/0163063 to Fernando et al., U.S. Pat. App. Pub. No. 2013/0192623 to Tucker et al., U.S. Pat. App. Pub. No. 2013/0298905 to Leven et al., U.S. Pat. App. Pub. No. 2013/0180553 to Kim et al., U.S. Pat. App. Pub. No. 2014/0000638 to Sebastian et al., U.S. Pat. App. Pub. No. 2014/0261495 to Novak et al., and U.S. Pat. App. Pub. No. 2014/0261408 to DePiano et al., all of which are incorporated herein by reference in their entireties.

FIG. 2 illustrates a perspective view of a suitable aerosol delivery device 200 that in some examples may correspond to the aerosol delivery device 100 of FIG. 1. As shown, the aerosol delivery device can comprise a control body 202 and a tank 204, which may correspond to respectively the control body 102 and tank 104 of FIG. 1. The control body may define an ergonomic shape configured to comfortably fit within a user's hand. The shape of the housing, however, is not limited and may be any shape that accommodates the various elements as described herein. In some implementations, the housing may be expressly non-cylindrical.

As previously explained, the tank 204 can be formed of a tank shell 206 enclosing a reservoir 208 therein. In some example implementations, the reservoir may be a refillable reservoir, and a container of aerosol precursor composition may be provided for refilling the reservoir. The tank and container may be removably, sealably connectable to one another such that the sealed coupling between the tank and the container may be configured to enable the transfer of aerosol precursor composition between the container and the aerosol delivery device.

FIGS. 3 and 4 illustrate a portion of a tank 300 of an aerosol delivery device that in some examples may correspond to the tank 204 of FIG. 2. As shown, the tank may include a tank shell 302, reservoir 304, and heater 306 that may correspond to respective ones of the tank shell 216, reservoir 218, and heater 222 of the tank 204 of FIG. 2. As more particularly shown in FIG. 3, the aerosol delivery device may include a connector 308 coupled to the tank shell (housing) and sealably connectable with a container of aerosol precursor composition for refilling the reservoir. The connector may be adapted to sealably connect with a suitable container of aerosol precursor composition in any of a number of different manners. Various mechanisms may connect the connector to the container such as a threaded engagement, a press-fit engagement, an interference fit, a magnetic engagement or the like.

In some examples, the container may include a nozzle with which the connector 308 may be sealably connectable. In this regard, in some examples, the connector may be configured to receive a standard (e.g., one centimeter) nozzle, or configured to mate with a corresponding manufacturer-specific nozzle. As shown in FIG. 4, the connector may include a body 400 integral with or coupled to a check valve 402 configured to control a flow of aerosol precursor composition from the container into the reservoir when the connector is sealably connected with the container. The check valve may control the flow of aerosol precursor composition by allowing the aerosol precursor composition to flow through it in only one direction.

In some examples, the body 400 of the connector 308 may define airflow ports 404*a*, 404*b* for the flow of air through the connector from the tank shell 302. More particularly, the airflow ports may be for the flow of air through the tank shell when the connector and the container are disengaged, such as during use of the aerosol delivery device. As used herein, a port may refer to a narrow and elongated passageway through which liquid, air, and the like may be transported. As illustrated, in one example implementation, the airflow ports may be substantially cylindrically shaped so as to allow for the smooth transfer of air. As illustrated the airflow ports may be arranged such that the flow path through the port is tortuous (e.g., including one or a plurality of turns) in order to preferentially allow the transport of aerosol and to prevent the transfer of the aerosol precursor out the mouthend. In other example implementations, further shapes and dimensions may be encompassed—e.g., a rectangular or triangular cross-section, multifaceted shapes, or the like.

In some example implementations, the connector 308 may further include a slot 406, defined by the body 400, and mateable with a matching tab 408 of the tank shell 302 to guide the connector into alignment with the tank shell, and more particularly, into alignment with a mouthpiece interface 410 of the tank shell, for coupling therewith.

In one example implementation, as illustrated in FIGS. 3 and 4, the check valve 402 is a diaphragm check valve including a flexible diagram sized to fit an opening 412 of the reservoir 304, and more particularly an opening within the mouthpiece interface 410, which defines an opening of the reservoir 304. The diaphragm check valve may define a naturally-closed passageway 414 that is configured to flex open and thereby allow through the passageway, the flow of aerosol precursor composition in response to at least a threshold positive pressure differential on a container-facing side of the flexible diaphragm when the connector is sealably connected with the container. In these implementations, transferring aerosol precursor composition includes transferring aerosol precursor composition from the container through the passageway of the diaphragm check valve and into the reservoir. Upon disengaging the connector and the container, and thereby relieving the pressure, the diaphragm check valve may automatically flex back to an original closed position. In these example implementations, the check valve may be formed of silicone, rubber, or another suitable material.

In an alternative implementation, the check valve 402 may be comprised of a flexible metal or alloy that may be coated with a thermoplastic elastomer such as silicone, rubber, or another suitable material. In another implementation, the check valve 402 may be a self-sealing and/or self-healing elastic material in which the aerosol precursor may be delivered through a conical, cylindrical, or needle shaped feature which may be inserted through the check valve, such that upon removal of the conical, cylindrical and/or needle shaped feature the check valve opening may close back upon itself due to the self-sealing and/or self-healing nature of the check valve material thereby preventing the escape of the aerosol precursor.

In some example implementations, the check valve 402 may be or include two or more components operatively coupled via a magnetic mechanism in which upon coupled the components effect a magnetic seal. In these implementations, upon the magnetic seal being broken, an opening is created to allow for the transfer of the aerosol precursor. The two or more components may be or include magnetic components (e.g., magnets) that may be contained within another material such as plastic, thermoplastic elastomer, or other suitable materials. The magnetic components may be electromagnets where, for example, a change in voltage across the magnetic component reduces the force in which the magnetic components are held in a sealed position. In these implementations, the aerosol precursor may be delivered through the arrangement of the sealed magnetic component that form a sealed interface to allow for the transfer of the aerosol precursor to the reservoir.

It should be noted that although example implementations of FIGS. 3 and 4 illustrate the connector 308 in which the check valve 402 is a diaphragm check valve, the connector may be embodied by various other forms including one or more one-way valves not expressly stated herein. For example, FIGS. 5A and 5B highlight one example of a suitable check valve 500 including a valve member movable by the container to open a passageway and thereby allow through the passageway, the flow of aerosol precursor composition when the connector is sealably connected with the container. More particularly, for example, the check valve 500 may be a swing check valve including a movable valve member or disc 502 sized to block a passageway 504 of the check valve from a transfer of aerosol precursor composition and swing open to allow the flow of aerosol precursor composition into the reservoir in response to the disc being displaced by the nozzle 506 of a container as the connector is sealably connected with the container, as shown in FIG. 5B.

FIGS. 6A and 6B highlight another example of a suitable check valve 600 in which the check valve includes a spring-loaded valve member 602 configured to open a passageway 604 and thereby allow through the passageway, the flow of aerosol precursor composition when the connector is sealably connected with the container. One example of a suitable check valve including a spring-loaded member is a ball check valve. Accordingly, the spring-loaded member may include a spherical ball. As shown in FIG. 6A, a depressible spring 606 may be naturally extended such that the ball blocks the passageway from transfer of aerosol precursor composition and thereby the flow of aerosol precursor composition into the reservoir (e.g., reservoir 304). As shown in FIG. 6B, the spring may be depressible as the connector is sealably connected with the container, and the ball may be thereby configured to open the passageway to allow the flow of aerosol precursor composition into the reservoir.

FIG. 7 illustrates yet another example of a suitable check valve 700 in which the check valve is a Tesla valve defining a channel 702 configured to allow the flow of aerosol precursor composition in only one direction, from the container into the reservoir. The Tesla valve may include a body defining a direction-dependent flow resistance, the one-way flow of aerosol precursor composition being based at least in part on direction-dependent flow resistance. As shown in FIG. 7, during engagement with a container, aerosol precursor composition may follow the forward flow direction 702*a* into the reservoir. In instances in which the aerosol delivery device is inverted, aerosol precursor composition flowing in the reverse direction 702*b* may encounter a different flow resistance as a result of the geometry of the connector, the direction-dependent flow resistance thereby preventing aerosol precursor composition from flowing out of the reservoir. The Tesla valve may not include any moving components, and thereby may be incorporated into a mold or fluid module of the aerosol delivery device. In some examples, the Tesla valve may be incorporated within micro-scale applications and may have greater reliability compared to check valves with moving parts (e.g., check valve 400, 500, 600). In other examples, multiple Tesla valves may be joined together in series to improve the direction-dependent flow of aerosol precursor.

As indicated above and further illustrated in FIG. 8, a mouthpiece 800 may be removably coupled to the at least one housing 304 of the aerosol delivery device. More particularly, the mouthpiece may be coupled to the mouthpiece interface 410 over the connector 308 such that the check valve 402 is exposed upon removal of the mouthpiece. The mouthpiece may correspond to the mouthpiece 224 of FIG. 2. In some examples, the connector may be positioned underneath the mouthpiece, and upon removal of the mouthpiece, the connector may be brought into direct engagement with the container.

FIG. 9 illustrates various operations in a method 900 of refilling an aerosol delivery device with aerosol precursor composition, according to an example implementation of the present disclosure. The aerosol delivery device may include at least one housing defining a refillable reservoir for storing aerosol precursor composition, and include a heating element configured to activate and vaporize components of the aerosol precursor composition stored in the reservoir in response to a flow of air through at least a portion of the at least one housing. The air may be combinable with a thereby formed vapor to form an aerosol. As shown in block 902, the method may include sealably connecting a connector of the aerosol delivery device with a container of aerosol precursor composition for refilling the reservoir. The connector may include a check valve controlling flow of aerosol precursor composition from the container into the reservoir when the connector is sealably connected with the container. As shown at block 904, the method may also include transferring aerosol precursor composition from the container through the check valve and into the reservoir to thereby refill the reservoir.

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in FIGS. 1-9 or as otherwise described above may be included in an aerosol delivery device according to the present disclosure.

Many modifications and other implementations of the disclosure set forth herein will come to mind to one skilled in the art to which these disclosure pertain having the benefit of the teachings presented in the foregoing descriptions and the associated drawings. Therefore, it is to be understood that the disclosure are not to be limited to the specific implementations disclosed and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. An aerosol delivery device comprising:

at least one housing defining a refillable reservoir for storing an aerosol precursor composition, the at least one housing including a mouthpiece interface within which an opening defines an opening of the reservoir;

a mouthpiece removably coupled to the mouthpiece interface;

a heating element contained within the at least one housing and configured to activate and vaporize components of the aerosol precursor composition in response to a flow of air through at least a portion of the at least one housing, the air being combinable with a thereby formed vapor to form an aerosol; and a connector coupled to the at least one housing, an exterior surface of the connector including a slot mateable with a matching tab on an interior surface of the at least one housing to guide the connector into alignment with the mouthpiece interface for coupling therewith, the mouthpiece being removably coupled to the mouthpiece interface over the connector, wherein the slot is a part of the connector, wherein the connector is sealably connectable with a container of aerosol precursor composition for refilling the reservoir, the connector including a check valve sized to fit the opening of the mouthpiece interface and thereby the opening of the reservoir, and configured to control a flow of aerosol precursor composition from the container into the reservoir when the mouthpiece is removed to expose the check valve, and the connector is sealably connected with the container.

2. The aerosol delivery device of claim 1, wherein the connector includes a body integral with or coupled to the check valve, the body defining an airflow port for the flow of air through the connector from at least the portion of the at least one housing, and wherein the body is a part of the connector.

3. The aerosol delivery device of claim 1, wherein the check valve is a diaphragm check valve including a flexible diaphragm sized to fit the opening of the mouthpiece interface and thereby the opening of the reservoir, the diaphragm defining a naturally-closed passageway that is configured to flex open and thereby allow through the passageway, the flow of aerosol precursor composition in response to at least a threshold positive pressure differential on a container-facing side of the flexible diaphragm when the connector is sealably connected with the container.

4. The aerosol delivery device of claim 1, wherein the check valve includes a valve member movable by the container to open a passageway and thereby allow through the passageway, the flow of aerosol precursor composition when the connector is sealably connected with the container.

5. The aerosol delivery device of claim 1, wherein the check valve includes a spring-loaded valve member configured to open a passageway and thereby allow through the passageway, the flow of aerosol precursor composition when the connector is sealably connected with the container.

6. The aerosol delivery device of claim 1, wherein the check valve is a Tesla valve or series of Tesla valves defining a channel configured to allow the flow of aerosol precursor composition in only one direction, from the container into the reservoir.

7. A method of refilling an aerosol delivery device with aerosol precursor composition, the aerosol delivery device including at least one housing defining a refillable reservoir for storing aerosol precursor composition, the at least one housing including a mouthpiece interface within which an opening defines an opening of the reservoir, the aerosol delivery device further including a mouthpiece removably coupled to the mouthpiece interface and including a heating element configured to activate and vaporize components of the aerosol precursor composition stored in the reservoir in response to a flow of air through at least a portion of the at least one housing, the air being combinable with a thereby formed vapor to form an aerosol, the method comprising:

aligning a connector of the aerosol delivery device with the mouthpiece interface for coupling therewith by using a slot on an exterior surface of the connector mateable with a matching tab on an interior surface of the at least one housing, the mouthpiece being removably coupled to the mouthpiece interface over the connector, wherein the slot is a part of the connector;

sealably connecting the connector with a container of aerosol precursor composition for refilling the reservoir, the connector including a check valve sized to fit the opening of the mouthpiece interface and thereby the opening of the reservoir, the check valve controlling flow of aerosol precursor composition from the container into the reservoir when the mouthpiece is removed to expose the check valve, and the connector is sealably connected with the container; and transferring aerosol precursor composition from the container through the check valve and into the reservoir to thereby refill the reservoir.

8. The method of claim 7, wherein the connector includes a body integral with or coupled to the check valve, the body defining an airflow port for the flow of air through the connector from at least the portion of the at least one housing, and wherein the body is a part of the connector.

9. The method of claim 7, wherein the check valve is a diaphragm check valve including a flexible diaphragm sized to fit the opening of the mouthpiece interface and thereby the opening of the reservoir and defining a naturally-closed passageway, and wherein transferring aerosol precursor composition includes causing at least a threshold positive pressure differential on a container-facing side of the flexible diaphragm to thereby cause the passageway to flex open and thereby allow through the passageway, the flow of aerosol precursor composition.

10. The method of claim 7, wherein the check valve includes a movable valve member, and sealably connecting the connector with the container includes the container moving the valve member to open a passageway and thereby allow through the passageway, the flow of aerosol precursor composition when the connector is sealably connected with the container.

11. The method of claim 7, wherein the check valve includes a spring-loaded valve member, and sealably connecting the connector with the container includes the valve member opening a passageway and thereby allowing through the passageway, the flow of aerosol precursor composition when the connector is sealably connected with the container.

12. The method of claim 7, wherein the check valve is a Tesla valve or series of Tesla valves defining a channel configured to allow the flow of aerosol precursor composition in only one direction, from the container into the reservoir, and wherein transferring aerosol precursor composition includes transferring aerosol precursor composition from the container through the channel and into the reservoir.

* * * * *